US009603363B2

(12) United States Patent
Lourdet

(10) Patent No.: US 9,603,363 B2
(45) Date of Patent: Mar. 28, 2017

(54) WEED CONTROL FROM APPLICATIONS OF AMINOPYRALID, TRICLOPYR, AND AN ORGANOSILICONE SURFACTANT

(71) Applicant: Dow AgroSciences LLC, Indianapolis, IN (US)

(72) Inventor: Yves Lourdet, Menotey (FR)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 14/134,411

(22) Filed: Dec. 19, 2013

(65) Prior Publication Data

US 2014/0179530 A1 Jun. 26, 2014

Related U.S. Application Data

(60) Provisional application No. 61/740,748, filed on Dec. 21, 2012.

(51) Int. Cl.
*A01N 43/40* (2006.01)
*A01N 25/30* (2006.01)

(52) U.S. Cl.
CPC ................... *A01N 43/40* (2013.01)

(58) Field of Classification Search
CPC combination set(s) only.
See application file for complete search history.

(56) References Cited

U.S. PATENT DOCUMENTS

| | | | |
|---|---|---|---|
| 5,561,099 A | 10/1996 | Murphy et al. | |
| 5,658,852 A | 8/1997 | Murphy et al. | |
| 6,297,197 B1 | 10/2001 | Fields et al. | |
| 7,314,849 B2 | 1/2008 | Balko et al. | |
| 7,432,227 B2 | 10/2008 | Balko et al. | |
| 7,786,044 B2 | 8/2010 | Epp et al. | |
| 7,863,220 B2 | 1/2011 | Clark et al. | |
| 8,309,491 B2 | 11/2012 | Li et al. | |
| 2005/0043182 A1 | 2/2005 | Douglass et al. | |
| 2007/0117721 A1 | 5/2007 | Keeney et al. | |
| 2008/0153704 A1 | 6/2008 | Yamaji et al. | |
| 2008/0248955 A1 | 10/2008 | Fowler et al. | |
| 2010/0016158 A1 | 1/2010 | Kilian et al. | |
| 2010/0069248 A1 | 3/2010 | Hacker et al. | |
| 2010/0190794 A1 | 7/2010 | Hupe et al. | |
| 2010/0273656 A1 | 10/2010 | Sedun et al. | |
| 2010/0279862 A1 | 11/2010 | Bickers et al. | |
| 2010/0285959 A1 | 11/2010 | Armel et al. | |
| 2011/0092367 A1 | 4/2011 | Griveau et al. | |
| 2011/0118120 A1 | 5/2011 | Corr et al. | |
| 2011/0136667 A1 | 6/2011 | Turner et al. | |
| 2011/0190130 A1 | 8/2011 | Garzon | |
| 2011/0251070 A1 | 10/2011 | Poffenberger et al. | |
| 2011/0294663 A1 | 12/2011 | Hacker et al. | |
| 2012/0015808 A1 | 1/2012 | Contreras et al. | |
| 2012/0053053 A1 | 3/2012 | Boussemghoune et al. | |
| 2012/0058899 A1 | 3/2012 | Jensen et al. | |
| 2012/0071320 A1 | 3/2012 | Atkinson et al. | |
| 2012/0115816 A1 | 5/2012 | Ramsay et al. | |
| 2012/0142532 A1 | 6/2012 | Wright et al. | |
| 2012/0149572 A1 | 6/2012 | Gewehr et al. | |
| 2014/0031214 A1 | 1/2014 | Yerkes et al. | |

FOREIGN PATENT DOCUMENTS

| | | |
|---|---|---|
| EP | 1314356 A1 | 5/2003 |
| EP | 1423001 | 11/2011 |
| WO | 9422311 A1 | 10/1994 |
| WO | 2007094836 A1 | 8/2007 |
| WO | 2009153247 | 12/2009 |
| WO | 2010017921 | 2/2010 |
| WO | 2010019377 | 2/2010 |
| WO | 2010046422 | 4/2010 |
| WO | 2010086437 | 8/2010 |
| WO | 2010149732 | 12/2010 |
| WO | 2011019652 | 2/2011 |
| WO | 2011113052 | 9/2011 |
| WO | 2012009489 | 1/2012 |
| WO | 2012018885 | 2/2012 |
| WO | 2012037425 | 3/2012 |
| WO | 2013026811 | 2/2013 |

OTHER PUBLICATIONS

IP 88909D, "Aminopyralid a new herbicide," ip.com, Mar. 4, 2005.*
Milestone label, Dow AgroSciences, Aug. 29, 2005.*
Garlon 4 label, Dow AgroSciences, Oct. 7, 2008.*
HCAPLUS abstract 1989:510930 (1989).*
HCAPLUS abstract 1992:250440 (1992).*
SILWET L-77 Marketing Bulletin, Momentive, 2011.*
Farm Chemical International, Crop Protection Database, "Aminopyralid," available at http://www.farmchemicalsinternational.com/crop-protection-database/#/product/detail/424163/ (accessed on May 28, 2014).
Bradley, K et al. "Response of biennial and perennial weeds to selected herbicides and prepackaged herbicide combinations in grass pastures and hay fields," HCAPLUS 2004:935205 (abstract).
Farm Chemical International, Crop Protection Database, "Triclopyr," available at http://www.farmchemicalsinternational.com/crop-protection-database/#/product/detail/402640/ (accessed on May 28, 2014).
International Search Report and Written Opinion issued Apr. 14, 2014, in related International Patent Application No. PCT/US2013/076626.

(Continued)

*Primary Examiner* — John Pak
(74) *Attorney, Agent, or Firm* — Michael R. Asam; Meunier Carlin & Curfman, LLC

(57) ABSTRACT

Disclosed herein are herbicidal compositions comprising a herbicidal effective amount of (a) aminopyralid, or an agriculturally acceptable salt or ester thereof, (b) triclopyr, or an agriculturally acceptable salt or ester thereof, and (c) an organosilicone surfactant. Also disclosed herein are methods of controlling undesirable vegetation, which comprise applying to vegetation or an area adjacent the vegetation or applying to soil or water to prevent the emergence or growth of vegetation (a) aminopyralid, or an agriculturally acceptable salt or ester thereof, (b) triclopyr, or an agriculturally acceptable salt or ester thereof, and (c) an organosilicone surfactant.

16 Claims, No Drawings

(56) References Cited

OTHER PUBLICATIONS

Tran, H. et al. "Assessment of herbicides for selectively controlling broom (Cystisus scoparius) growing with Pinus radiata" 17th Australasian Weeds Conference, New Zealand Plant Protection Society, Sep. 26-30, 2010; p. 372.
Tomlin, C. D. S., Ed., The Pesticide Manual: A World Compendium, "Aminopyralid," 15th ed., BCPC: Alton, 2009, pp. 34-35.
Tomlin, C. D. S., Ed., The Pesticide Manual: A World Compendium, "Triclopyr," 15th ed., BCPC: Alton, 2009, pp. 1161-1163.
Extended European Search Report Issued in Application No. PCT/US2013076626 dated Jun. 21, 2016.
Bollig, et al., "Effect of plant moisture stress and application surface on uptake and translocation to tricopyr with organosilicone surfactant in red maple seedlings", Canadian J of Forest Research, 1995, 425-429.
Buick, et al., "The mechanism of organosilicone surfactant-induced uptakae of amine and ester formulations of triclopyr", 1st Int Weed Control Conf, 14992, 103-105.

* cited by examiner

WEED CONTROL FROM APPLICATIONS OF AMINOPYRALID, TRICLOPYR, AND AN ORGANOSILICONE SURFACTANT

CROSS REFERENCE TO RELATED APPLICATIONS

This application claims the benefit of U.S. Provisional Patent Application Ser. No. 61/740,748 filed Dec. 21, 2012, the disclosure of which is expressly incorporated herein by reference.

FIELD OF THE DISCLOSURE

The present disclosure relates to herbicidal compositions comprising a herbicidal effective amount of (a) aminopyralid or an agriculturally acceptable salt or ester thereof, (b) triclopyr or an agriculturally acceptable salt or ester thereof, and (c) an organosilicone surfactant. The present disclosure also relates to methods for controlling undesirable vegetation.

BACKGROUND

Many recurring problems in agriculture involve controlling growth of undesirable vegetation that can, for instance, inhibit crop growth. To help control undesirable vegetation, researchers have produced a variety of chemicals and chemical formulations effective in controlling such unwanted growth. However, a continuing need exists for new compositions and methods to control growth of undesirable vegetation, particularly over extended periods of time.

SUMMARY OF THE DISCLOSURE

Additives can be added to herbicidal compositions to improve efficacy. For example, surfactants can be added to post-emergent herbicidal compositions to reduce the surface tension of the composition. By reducing the composition's surface tension, the spray coverage and penetration of the composition on leaf surfaces can be increased; at the same time, the evaporation rate of the composition can be reduced. This can have the effect of increasing the amount of herbicide that translocates into a target plant, and increasing the herbicidal efficacy of the composition in the short term.

While surfactants can be added to improve the short term efficacy of herbicidal compositions (e.g., by increasing plant uptake at the time of herbicide application), surfactants are not generally known to improve the efficacy of herbicidal compositions over the long term. The present disclosure is based on the unexpected discovery that (a) aminopyralid or an agriculturally acceptable salt or ester thereof, (b) triclopyr or an agriculturally acceptable salt or ester thereof, and (c) an organosilicone surfactant display increased herbicidal over activity over extended periods of time relative to (a) and (b) administered in the absence of (c).

Accordingly, the present disclosure relates to herbicidal compositions comprising a herbicidal effective amount of (a) aminopyralid, or an agriculturally acceptable salt or ester thereof, (b) triclopyr, or an agriculturally acceptable salt or ester thereof, and (c) an organosilicone surfactant. The acid equivalent weight ratio of (a) to (b) can be from 1:2 to 1:20 (e.g., from 1:7 to 1:10). In certain embodiments, the weight ratio of (c) (in grams active ingredient per hectare (g ai/ha)) to (a) (in grams acid equivalent per hectare (g ae/ha)) and (b) (in g ae/ha) in combination can be from 1:1 to 1:8.

In some embodiments, the organosilicone surfactant is defined by Formula I

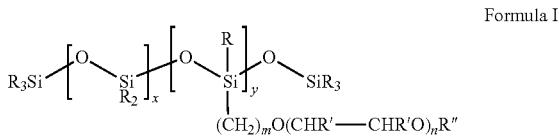

Formula I wherein
x is an integer from 0 to 100;
y is an integer from 1 to 30;
m is, independently for each occurrence, an integer from 1 to 20;
n is, independently for each occurrence, an integer from 1 to 30;
R is, independently for each occurrence, hydrogen or a $C_1$-$C_6$ hydrocarbyl group;
R' is, independently for each occurrence, hydrogen or a $C_1$-$C_4$ hydrocarbyl group; and
R" is, independently for each occurrence, hydrogen, a $C_1$-$C_{20}$ hydrocarbyl group, or an acyl group.

In some embodiments, the organosilicone surfactant is a modified trisiloxane. Examples of modified trisiloxane surfactants include alkyl-modified trisiloxanes, alkoxylated trisiloxanes, and polyalkyleneoxide-modified trisiloxanes.

In certain embodiments, the organosilicone surfactant is polyalkyleneoxide-modified heptamethyltrisiloxane defined by Formula II

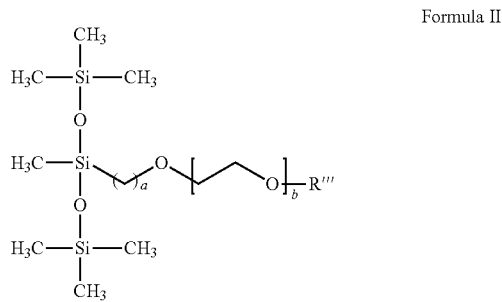

Formula II wherein
a is an integer ranging from 1 to 10;
b is an integer ranging from 1 to 30; and
R''' is hydrogen, a $C_1$-$C_{20}$ hydrocarbyl group, or an acyl group.

The present disclosure also relates to methods of controlling undesirable vegetation, which comprise applying to vegetation or an area adjacent the vegetation or applying to soil or water to prevent the emergence or growth of vegetation a herbicidally effective amount of (a) aminopyralid or an agriculturally acceptable salt or ester thereof, (b) triclopyr or an agriculturally acceptable salt or ester thereof, and (c) an organosilicone surfactant. In some embodiments, (a), (b), and (c) are applied simultaneously. In some embodiments, (a), (b), and (c) are applied post-emergence of the undesirable vegetation.

The compositions and methods disclosed herein can be used to control undesired vegetation in a variety of crop and non-crop applications. Exemplary non-crop areas include, but are not limited to, turfgrass, pastures, grasslands, rangelands, fallow land, rights-of-way, aquatic settings, tree and vine, wildlife management areas, non-irrigation ditchbanks, and forests. In some embodiments, the compositions and methods disclosed herein can be used in industrial vegetation management (IVM), for example, to control undesired vegetation along roadsides, power-lines, pipelines, rights-of-way, railways, well sites, and equipment yards. In some embodiments, the compositions and methods disclosed herein can also be used in forestry (e.g., for site preparation or for combating undesirable vegetation in plantation forests). In some embodiments, the compositions and methods disclosed herein can be used to control undesirable vegetation in conservation reserve program lands (CRP), trees, vines, grasslands, and grasses grown for seed. In some embodiments, the compositions and methods disclosed herein can be used on lawns (e.g., residential, industrial, and institutional), golf courses, parks, cemeteries, athletic fields, and sod farms. In some embodiments, the compositions and methods disclosed herein are used to control undesired vegetation in a crop, such as rice. The composition can be effective for an extended period such that the undesirable vegetation is controlled for a period of at least 180 days after application or at least 300 days after application.

The undesirable vegetation can be a broadleaf weed, a sedge weed, a woody plant, a semi-woody plant, or combination thereof. In some cases, the undesirable vegetation is selected from gorse (*Ulex europaeus*, ULEEU), blackthorn (*Prunus spinosa*, PRNSN), species of ash (*Fraxinus* sp., FRXSS), bloody-twig dogwood (*Cornus sanguine*, CRWSA), species of the genus *Carex* (*Carex* sp., CRXSS), Scotch broom (*Cytisus scoparius*, SAOSC), common hawthorn (*crataegus monogyna*, CSCMO), and combinations thereof.

In some embodiments, (a) is applied in an amount of from 5-85 grams acid equivalent per hectare (g ae/ha) (e.g., from 25-65 g ae/ha). In some embodiments, (b) is applied in an amount of from 10-500 g ae/ha (e.g., from 250-400 g ae/ha). In some embodiments, (c) is applied in an amount of from 50-300 grams active ingredient per hectare (g ai/ha) (e.g., from 150-180 g ai/ha).

The description below sets forth details of one or more embodiments of the present disclosure. Other features, objects, and advantages will be apparent from the description and from the claims.

DETAILED DESCRIPTION

The present disclosure relates to herbicidal compositions comprising (a) aminopyralid or an agriculturally acceptable salt or ester thereof, (b) triclopyr or an agriculturally acceptable salt or ester thereof, and (c) an organosilicone surfactant. The present disclosure also relates to methods for controlling undesirable vegetation.

The term "herbicide," as used herein, means an active ingredient that kills, controls, or otherwise adversely modifies the growth of vegetation. A "herbicidally effective amount" is an amount of an active ingredient that causes a "herbicidal effect," i.e., an adversely modifying effect and includes deviations from, for instance, natural development, killing, regulation, desiccation, and retardation. The terms "plants" and "vegetation" can include, for instance, germinant seeds, emerging seedlings, and established vegetation.

Aminopyralid

Compositions and methods of the present disclosure can include aminopyralid (i.e., 4-amino-3,6-dichloropyridine-2-carboxylic acid or 4-amino-3,6-dichloropicolinic acid) or an agriculturally acceptable salt or ester thereof. Aminopyralid is a synthetic auxin herbicide used to control broadleaf weeds in rangelands, pastures, and industrial settings (e.g., roadside, power-line, pipeline, right-of-way, railway, well site, equipment yard, or non-crop land).

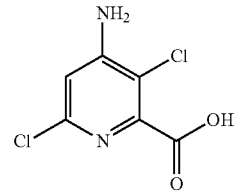 [SMILES: Nc1cc(Cl)nc(C(=O)O)c1Cl]

Aminopyralid can be provided in its acid form (as shown above), or as an agriculturally acceptable salt or ester thereof. Exemplary agriculturally acceptable salts of aminopyralid include, but are not limited to, sodium salts, potassium salts, ammonium salts or substituted ammonium salts, in particular mono-, di-, and tri-$C_1$-$C_8$-alkylammonium salts such as methyl ammonium, dimethylammonium, triethylammonium, and isopropylammonium, mono-, di- and tri-hydroxy-$C_2$-$C_8$-alkylammonium salts such as hydroxyethylammonium, di(hydroxyethyl)ammonium, tri(hydroxyethyl)ammonium, hydroxypropylammonium, di(hydroxypropyl)ammonium and tri(hydroxypropyl)ammonium salts, triisopropanolammonium salts, olamine salts, and diglycolamine salts. Exemplary agriculturally acceptable salts of aminopyralid include aminopyralid-potassium and aminopyralid-triisoproanolammonium.

In some embodiments, aminopyralid is provided as an agriculturally acceptable ester. Suitable esters include, but are not limited to, $C_1$-$C_8$-alkyl esters and $C_1$-$C_4$-alkoxy-$C_2$-$C_4$-alkyl esters, such as methyl esters, ethyl esters, isopropyl, butyl, hexyl, heptyl, isoheptyl, isooctyl, butotyl, 2-ethylhexyl and butoxyethyl esters, and aryl esters such as benzyl.

Aminopyralid, as well as methods of making and using thereof, are known in the art. See, for example, U.S. Pat. No. 6,297,197 to Fields, et al. The herbicidal activity of aminopyralid is described, for example, in Tomlin, C. D. S., Ed. *The Pesticide Manual: A World Compendium*, 15$^{th}$ ed.; BCPC: Alton, 2009 (hereafter "The Pesticide Manual, Fifteenth Edition, 2009") Aminopyralid or an agriculturally acceptable salt or ester thereof is or has been commercially available, for example, from Dow AgroSciences, LLC under the trademark MILESTONE®.

Aminopyralid or an agriculturally acceptable salt or ester thereof can be applied to vegetation or an area adjacent the vegetation or applied to soil or water to prevent the emergence or growth of vegetation in an amount sufficient to induce a herbicidal effect. In some embodiments, the aminopyralid or agriculturally acceptable salt or ester thereof is applied to vegetation or an area adjacent the vegetation or applied to soil or water to prevent the emergence or growth of vegetation in an amount of 5 g ae/ha or greater (e.g., 7.5 g ae/ha or greater, 10 g ae/ha or greater, 12.5 g ae/ha or greater, 15 g ae/ha or greater, 17.5 g ae/ha or greater, 20 g ae/ha or greater, 25 g ae/ha or greater, 30 g ae/ha or greater, 35 g ae/ha or greater, 40 g ae/ha or greater, 45 g ae/ha or greater, 50 g ae/ha or greater, 55 g ae/ha or greater, 60 g ae/ha or greater, 65 g ae/ha or greater, 70 g ae/ha or greater, 75 g ae/ha or greater, or 80 g ae/ha or greater). In some embodiments, the aminopyralid or agriculturally acceptable salt or ester thereof is applied to vegetation or an area adjacent the vegetation or applied to soil or water to prevent the emergence or growth of vegetation in an amount of 85 g ae/ha or less (e.g., 80 g ae/ha or less, 75 g ae/ha or less, 70 g ae/ha or less, 65 g ae/ha or less, 60 g ae/ha or less, 55 g ae/ha or less, 50 g ae/ha or less, 45 g ae/ha or less, 40 g ae/ha or less, 35 g ae/ha or less, 30 g ae/ha or less, 25 g ae/ha or less, 20 g ae/ha or less, 17.5 g ae/ha or less, 15 g ae/ha or less, 12.5 g ae/ha or less, 10 g ae/ha or less, or 7.5 g ae/ha or less).

Aminopyralid or an agriculturally acceptable salt or ester thereof can be applied to vegetation or an area adjacent the vegetation or applied to soil or water to prevent the emergence or growth of vegetation in an amount ranging from any of the minimum values described above to any of the maximum values described above. In some embodiments, the aminopyralid or agriculturally acceptable salt or ester thereof is applied to vegetation or an area adjacent the vegetation or applied to soil or water to prevent the emergence or growth of vegetation in an amount of from 5-85 g ae/ha (e.g., from 10-80 g ae/ha, from 15-75 g ae/ha, from 20-70 g ae/ha, or from 25-65 g ai/ha).

Triclopyr

Compositions and methods of the present disclosure can include triclopyr (i.e., 3,5,6-trichloro-2-pyridinyloxyacetic acid) or an agriculturally acceptable salt or ester thereof. Triclopyr is a synthetic auxin herbicide used to control woody plants and broadleaf weeds in turf, pastures, rangeland, non-irrigation ditchbanks, forests, and industrial settings (e.g., roadside, power-line, pipeline, right-of-way, railway, well site, equipment yard, or non-crop land). Triclopyr can also be used as an aquatic herbicide.

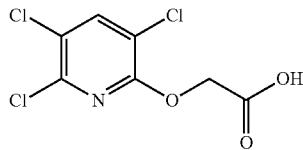 [SMILES: O=C(O)COc1nc(Cl)c(Cl)cc1Cl]

Triclopyr can be provided in its acid form (as shown above), or as an agriculturally acceptable salt or ester thereof. Exemplary agriculturally acceptable salts of triclopyr include, but are not limited to, sodium salts, potassium salts, ammonium salts or substituted ammonium salts, in particular mono-, di-, and tri-$C_1$-$C_8$-alkylammonium salts such as methyl ammonium, dimethylammonium, triethylammonium, and isopropylammonium, mono-, di- and tri-hydroxy-$C_2$-$C_8$-alkylammonium salts such as hydroxyethylammonium, di(hydroxyethyl)ammonium, tri(hydroxyethyl)ammonium, hydroxypropylammonium, di(hydroxypropyl)ammonium and tri(hydroxypropyl)ammonium salts, triisopropanolammonium salts, olamine salts, and diglycolamine salts. Exemplary agriculturally acceptable salts of triclopyr include triclopyr-triethylammonium. In some embodiments, triclopyr is provided as an agriculturally acceptable ester. Suitable esters include, but are not limited to, $C_1$-$C_8$-alkyl esters and $C_1$-$C_4$-alkoxy-$C_2$-$C_4$-alkyl esters, such as methyl esters, ethyl esters, isopropyl, butyl, hexyl, heptyl, isoheptyl, isooctyl, butotyl, 2-ethylhexyl and butoxyethyl esters, and aryl esters such as benzyl. Exemplary agriculturally acceptable esters of triclopyr include triclopyr-butotyl.

The herbicidal activity of triclopyr is described, for example, in *The Pesticide Manual*, Fifteenth Edition, 2009. Triclopyr or agriculturally acceptable salts or esters thereof are or have been commercially available, for example, under the trademarks REFUTE® (by Albaugh, Inc.), CROSSROAD® (by Albaugh, Inc.), TRIBEL® (by Chimac-Agriphar S.A.), GARLON® (by Dow AgroSciences LLC), GRANDSTAND® (by Dow AgroSciences LLC), GRANDSTAND R® (by Dow AgroSciences LLC), PATHFINDER® (by Dow AgroSciences LLC), PATHFINDER II® (by Dow AgroSciences LLC), REMEDY® (by Dow AgroSciences LLC), TURFLON® (by Dow AgroSciences LLC), TURFLON ESTER ULTRA® (by Dow AgroSciences LLC), FERLON® (by Fertiagro Pte. Ltd.), RELEGATE® (by Nufarm Americas, Inc.), CRYSTAL TRICLOPYR® (by Dupocsa, Protectores Quimicos para el Campo S.A.), TRYCERA® (by Helena Chemical Co.), RENOVATE 3® (by SePRO Corp.), RENOVATE MAX G® (by SePRO Corp.), and RENOVATE OTF® (by SePRO Corp.).

The triclopyr or an agriculturally acceptable salt or ester thereof can be used in an amount sufficient to induce a herbicidal effect. In some embodiments, the triclopyr or agriculturally acceptable salt or ester thereof is applied to vegetation or an area adjacent the vegetation or applied to soil or water to prevent the emergence or growth of vegetation in an amount of 10 g ae/ha or greater (e.g., 15 g ae/ha or greater, 20 g ae/ha or greater, 25 g ae/ha or greater, 30 g ae/ha or greater, 40 g ae/ha or greater, 50 g ae/ha or greater, 60 g ae/ha or greater, 70 g ae/ha or greater, 75 g ae/ha or greater, 80 g ae/ha or greater, 90 g ae/ha or greater, 100 g ae/ha or greater, 110 g ae/ha or greater, 120 g ae/ha or greater, 125 g ae/ha or greater, 130 g ae/ha or greater, 140 g ae/ha or greater, 150 g ae/ha or greater, 160 g ae/ha or greater, 170 g ae/ha or greater, 175 g ae/ha or greater, 180 g ae/ha or greater, 190 g ae/ha or greater, 200 g ae/ha or greater, 210 g ae/ha or greater, 220 g ae/ha or greater, 225 g ae/ha or greater, 230 g ae/ha or greater, 240 g ae/ha or greater, 250 g ae/ha or greater, 260 g ae/ha or greater, 270 g ae/ha or greater, 275 g ae/ha or greater, 280 g ae/ha or greater, 290 g ai/ha or greater, 300 g ae/ha or greater, 310 g ae/ha or greater, 320 g ae/ha or greater, 325 g ae/ha or greater, 330 g ae/ha or greater, 340 g ae/ha or greater, 350 g ae/ha or greater, 360 g ae/ha or greater, 370 g ae/ha or greater, 375 g ae/ha or greater, 380 g ae/ha or greater, 390 g ae/ha or greater, 400 g ae/ha or greater, 410 g ae/ha or greater, 420 g ae/ha or greater, 425 g ae/ha or greater, 430 g ae/ha or greater, 440 g ae/ha or greater, 450 g ae/ha or greater, 460 g ae/ha or greater, 470 g ae/ha or greater, 475 g ae/ha or greater, 480 g ae/ha or greater, or 490 g ae/ha or greater). In some embodiments, the triclopyr or agriculturally acceptable salt or ester thereof is applied to vegetation or an area adjacent the vegetation or applied to soil or water to prevent the emergence or growth of vegetation in an amount of 500 g ae/ha or less (e.g., 490 g ae/ha or less, 480 g ae/ha or less, 475 g ae/ha or less, 470 g ae/ha or less, 460 g ae/ha or less, 450 g ae/ha or less, 440 g ae/ha or less, 430 g ae/ha or less, 425 g ae/ha or less, 420 g ae/ha or less, 410 g ae/ha or less, 400 g ae/ha or less, 390 g ae/ha or less, 380 g ae/ha or less, 375 g ae/ha or less, 370 g ae/ha or less, 360 g ae/ha or less, 350 g ae/ha or less, 340 g ae/ha or less, 330 g ae/ha or less, 325 g ae/ha or less, 320 g ae/ha or less, 310 g ae/ha or less, 300 g ae/ha or less, 290 g ae/ha or less, 280 g ae/ha or less, 275 g ae/ha or less, 270 g ae/ha or less, 260 g ae/ha or less, 250 g ae/ha or less, 240 g ae/ha or less, 230 g ae/ha or less, 225 g ae/ha or less, 220 g ae/ha or less, 210 g ae/ha or less, 200 g ae/ha or less, 190 g ae/ha or less, 180 g ae/ha or less, 175 g ae/ha or less, 170 g ae/ha or less, 160 g ae/ha or less, 150 g ae/ha or less, 140 g ae/ha or less, 130 g ae/ha or less, 125 g ae/ha or less, 120 g ae/ha or less, 110 g ae/ha or less, 100 g ae/ha or less, 90 g ae/ha or less, 80 g ae/ha or less, 75 g ae/ha or less, 70 g ae/ha or less, 60 g ae/ha or less, 50 g ae/ha or less, 40 g ae/ha or less, 30 g ae/ha or less, 25 g ae/ha or less, 20 g ae/ha or less, or 15 g ae/ha or less).

Triclopyr or an agriculturally acceptable salt or ester thereof can be applied to vegetation or an area adjacent the vegetation or applied to soil or water to prevent the emergence or growth of vegetation in an amount ranging from any of the minimum values described above to any of the maximum values described above. In some embodiments, the triclopyr or agriculturally acceptable salt or ester thereof is applied to vegetation or an area adjacent the vegetation or applied to soil or water to prevent the emergence or growth of vegetation in an amount of from 10-500 g ae/ha (e.g., from 25-480 g ae/ha, from 50-475 g ae/ha, from 100-450 g ae/ha, from 150-440 g ae/ha, from 200-425 g ae/ha, or from 250-400 g ae/ha).

Organosilicone Surfactants

Compositions and methods of the present disclosure can include an organosilicone surfactant.

The organosilicone surfactant can be non-ionic. In some embodiments, the organosilicone surfactant has an HLB (Hydrophilic/Lipophilic Balance) number ranging from 5 to 15 (e.g., from 8 to 12, or from 9.5 to 11.5).

In some embodiments, the organosilicone surfactant is defined by Formula I

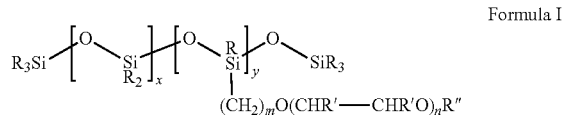

Formula I wherein
- x is an integer from 0 to 100;
- y is an integer from 1 to 30;
- m is, independently for each occurrence, an integer from 1 to 20;
- n is, independently for each occurrence, an integer from 1 to 30;
- R is, independently for each occurrence, hydrogen or a $C_1$-$C_6$ hydrocarbyl group;
- R' is, independently for each occurrence, hydrogen or a $C_1$-$C_4$ hydrocarbyl group; and
- R" is, independently for each occurrence, hydrogen, a $C_1$-$C_{20}$ hydrocarbyl group, or an acyl group.

In some embodiments of Formula I, x is an integer from 0 to 25 (e.g., from 0 to 20, from 0 to 15, from 0 to 10, or from 0 to 5). In certain embodiments of Formula I, x is 0. In certain embodiments of Formula I, x is greater than 0.

In some embodiments, y is an integer from 1 to 20 (e.g., from 1 to 15, from 1 to 10, or from 1 to 5). In certain embodiments of Formula I, y is 1.

In some embodiments of Formula I, x is 0 and y is 1 (i.e., the organosilicone surfactant is a trisiloxane).

In some embodiments of Formula I, R is, in every occurrence, a $C_1$-$C_4$ hydrocarbyl group. In certain embodiments of Formula I, R is, in every occurrence, a methyl group.

In some instances of Formula I, x is 0; y is 1; and R is, in every occurrence, a methyl group.

In some embodiments of Formula I, m is an integer ranging from 2 to 8, and n is an integer ranging from 1 to 20 (e.g., from 2 to 15, from 4 to 12, from 5 to 10, or from 6 to 9).

In certain embodiments of Formula I, R' is, in each occurrence, hydrogen.

In certain embodiments of Formula I, R" is hydrogen or methyl.

In some embodiments, the organosilicone surfactant is a modified trisiloxane. Examples of modified trisiloxane surfactants include alkyl-modified trisiloxanes, alkoxylated trisiloxanes, and polyalkyleneoxide-modified trisiloxanes.

In certain embodiments, the organosilicone surfactant is polyalkyleneoxide-modified heptamethyltrisiloxane defined by Formula II

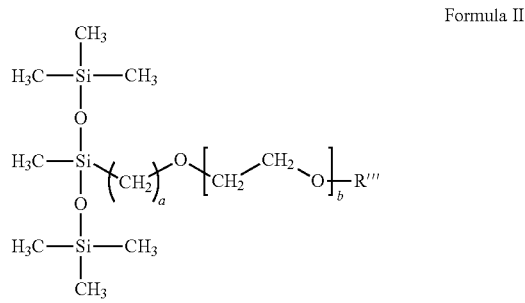

Formula II wherein
- a is an integer ranging from 1 to 10;
- b is an integer ranging from 1 to 30; and
- R'" is hydrogen, a $C_1$-$C_{20}$ hydrocarbyl group, or an acyl group.

In some embodiments of Formula II, a is an integer ranging from 2 to 5. In certain embodiments of Formula II, a is 3.

In some embodiments of Formula II, b is an integer ranging from 1 to 20 (e.g., from 2 to 15, from 4 to 12, from 5 to 10, or from 6 to 9).

In some embodiments of Formula II, R'" is a hydrogen or a $C_1$-$C_4$ hydrocarbyl group.

In certain embodiments of Formula II, a is 3, b is an integer ranging from 5 to 10, and R'" is hydrogen or methyl.

In certain embodiments of Formula II, a is 3, b is an integer ranging from 7 to 8, and R'" is methyl.

Polyalkyleneoxide-modified trisiloxane surfactants of this type are known in the art, and are or have been commercially available, for example, under the trademarks SILWET® L-77 (by Momentive Performance Materials, Inc.) and SILWET® 408 (by Momentive Performance Materials, Inc.).

Alkyl-modified trisiloxane surfactants are also known in the art. See, for example, U.S. Pat. Nos. 5,561,099 and 5,658,852 to Murphy, et al. Alkyl-modified trisiloxanes are or have been commercially available, for example, under the trademark SILWET® 560 (by Momentive Performance Materials, Inc.).

Alkoxylated trisiloxane surfactants are also known in the art and are or have been commercially available, for example, under the trademarks SILWET® 618 (by Momentive Performance Materials, Inc.), SILWET® 625 (by Momentive Performance Materials, Inc.), SILWET® 719 (by Momentive Performance Materials, Inc.), and SILWET® 806 (by Momentive Performance Materials, Inc.).

With reference to the formulae above, the term "hydrocarbyl," as used herein, refers to a univalent group formed from a hydrocarbon by removal of a hydrogen atom; e.g., methyl (from methane). Examples of hydrocarbyl moieties include, for example, alkyl, alkenyl, alkynyl, and aryl moieties. Hydrocarbyl moieties also include alkyl, alkenyl, alkynyl, and aryl moieties substituted with other aliphatic or cyclic hydrocarbon groups, such as alkylaryl, alkenylaryl and alkynylaryl. Hydrocarbyl moieties can be optionally substituted with between 1 and 4 hydroxy groups. In some embodiments, hydrocarbyl moieties comprise from 1 to 20 carbon atoms (e.g., from 1 to 12 carbon atoms, from 1 to 8 carbon atoms, from 1 to 7 carbon atoms, from 1 to 6 carbon atoms, or from 1 to 4 carbon atoms). In some embodiments, hydrocarbyl moieties comprise alkyl groups comprising from 1 to 8 carbon atoms (e.g., from 1 to 6 carbon atoms or from 1 to 4 carbon atoms). In some embodiments, the hydrocarbyl moieties comprise aryl groups comprising from 5 to 7 carbon atoms.

With reference to the formulae above, the term "acyl," as used herein, refers to a moiety formed by removal of the hydroxy group from the group —COOH (i.e., a carboxylic acid). For example, acyl moieties can be defined by $RC(O)$—, wherein R is hydrocarbyl, $R^1O$—, $R^2R^2N$—, or $R^1S$—; $R^1$ is hydrocarbyl; and $R^2$ is, independently for each occurrence, hydrogen or hydrocarbyl.

The organosilicone surfactant can be used in an amount sufficient to enhance the herbicidal efficacy of (a) and (b) over extended periods of time, relative to the efficacy of (a) and (b) administered in the absence of (c). In some embodiments, the organosilicone surfactant is applied to vegetation or an area adjacent the vegetation or applied to soil or water to prevent the emergence or growth of vegetation in an amount of 50 g ai/ha or greater (e.g., 60 g ai/ha or greater, 70 g ai/ha or greater, 80 g ai/ha or greater, 90 g ai/ha or greater, 100 g ai/ha or greater, 110 g ai/ha or greater, 120 g ai/ha or greater, 130 g ai/ha or greater, 140 g ai/ha or greater, 150 g ai/ha or greater, 160 g ai/ha or greater, 170 g ai/ha or greater, 180 g ai/ha or greater, 190 g ai/ha or greater, 200 g ai/ha or greater, 210 g ai/ha or greater, 220 g ai/ha or greater, 230 g ai/ha or greater, 240 g ai/ha or greater, 250 g ai/ha or greater, 260 g ai/ha or greater, 270 g ai/ha or greater, 280 g ai/ha or greater, or 290 g ai/ha or greater). In some embodiments, the organosilicone surfactant is applied to vegetation or an area adjacent the vegetation or applied to soil or water to prevent the emergence or growth of vegetation in an amount of 300 g ai/ha or less (e.g., 290 g ai/ha or less, 280 g ai/ha or less, 270 g ai/ha or less, 260 g ai/ha or less, 250 g ai/ha or less, 240 g ai/ha or less, 230 g ai/ha or less, 220 g ai/ha or less, 210 g ai/ha or less, 200 g ai/ha or less, 190 g ai/ha or less, 180 g ai/ha or less, 170 g ai/ha or less, 160 g ai/ha or less, 150 g ai/ha or less, 140 g ai/ha or less, 130 g ai/ha or less, 120 g ai/ha or less, 110 g ai/ha or less, 100 g ai/ha or less, 90 g ai/ha or less, 80 g ai/ha or less, 70 g ai/ha or less, or 60 g ai/ha or less).

The organosilicone surfactant can be applied to vegetation or an area adjacent the vegetation or applied to soil or water to prevent the emergence or growth of vegetation in an amount ranging from any of the minimum values described above to any of the maximum values described above. In some embodiments, the organosilicone surfactant is applied to vegetation or an area adjacent the vegetation or applied to soil or water to prevent the emergence or growth of vegetation in an amount of from 50-300 g ai/ha (e.g., from 60-280 g ai/ha, from 80-260 g ai/ha, from 100-250 g ai/ha, from 110-230 g ai/ha, from 130-200 g ai/ha, or from 150-180 g ai/ha). In some embodiments, the organosilicone surfactant can be applied to vegetation or an area adjacent the vegetation or applied to soil or water to prevent the emergence or growth of vegetation at a rate ranging from 0.025% to 0.15% by volume.

Herbicidal Mixtures or Combinations

The (a) aminopyralid or an agriculturally acceptable salt or ester thereof, (b) triclopyr or an agriculturally acceptable salt or ester thereof, and (c) an organosilicone surfactant are mixed together or applied in combination in a herbicidally effective amount.

In some embodiments, the compositions and methods disclosed herein can be mixed together or applied in combination in an effective amount to control undesired vegetation over an extended period of time (e.g., for a period of at least 180 days after application). In some embodiments, the compositions and methods disclosed herein can, based on the individual components, be used at lower application rates to achieve a herbicidal effect comparable to the effect produced by the individual components at normal application rates. In some embodiments, the compositions and methods disclosed herein provide an accelerated action on undesired vegetation (i.e., they effect damaging of undesired vegetation more quickly compared with application of the individual herbicides).

In some embodiments, the acid equivalent weight ratio of (a) aminopyralid or agriculturally acceptable salt or ester thereof to (b) triclopyr or an agriculturally acceptable salt or ester thereof is at least 1:20 (e.g., at least 1:19, at least 1:18, at least 1:17, at least 1:16, at least 1:15, at least 1:14, at least 1:13, at least 1:12, at least 1:11, at least 1:10, at least 1:9, at least 1:8, at least 1:7, at least 1:6, at least 1:5, at least 1:4, or at least 1:3). In some embodiments, the acid equivalent weight ratio of (a) to (b) is 1:2 or less (e.g., 1:3 or less, 1:4 or less, 1:5 or less, 1:6 or less, 1:7 or less, 1:8 or less, 1:9 or less, 1:10 or less, 1:11 or less, 1:12 or less, 1:13 or less, 1:14 or less, 1:15 or less, 1:16 or less, 1:17 or less, 1:18 or less, or 1:19 or less).

The acid equivalent weight ratio of (a) aminopyralid or agriculturally acceptable salt or ester thereof to (b) triclopyr or an agriculturally acceptable salt or ester thereof can range from any of the minimum ratios described above to any of the maximum ratios described above. In some embodiments, the acid equivalent weight ratio of (a) to (b) is from 1:20 to 1:2 (e.g., from 1:18 to 1:4, from 1:15 to 1:5, from 1:12 to 1:6, or from 1:10 to 1:7).

In some embodiments, the weight ratio of (c) (in g ai/ha) to (a) (in g ae/ha) and (b) (in g ae/ha) in combination (i.e., (c):(a)+(b)) is at least 1:8 (e.g., at least 1:7, at least 1:6, at least 1:5, at least 1:4, at least 1:3, or at least 1:2). In some embodiments, the weight ratio of (c) (in g ai/ha) to (a) (in g ae/ha) and (b) (in g ae/ha) in combination is 1:1 or less (e.g., 1:2 or less, 1:3 or less, 1:4 or less, 1:5 or less, 1:6 or less, or 1:7 or less).

The weight ratio of (c) (in g ai/ha) to (a) (in g ae/ha) and (b) (in g ae/ha) in combination can range from any of the minimum ratios described above to any of the maximum ratios described above. In some embodiments, the weight ratio of (c) (in g ai/ha) to (a) (in g ae/ha) and (b) (in g ae/ha) in combination is from 1:8 to 1:1 (e.g., from 1:6 to 1:1.5 or from 1:5 to 1:2).

Formulations

The present disclosure also relates to formulations of the compositions and methods disclosed herein. In some embodiments, the formulation can be in the form of a single package formulation including (a) aminopyralid or an agriculturally acceptable salt or ester thereof, (b) triclopyr or an agriculturally acceptable salt or ester thereof, and (c) an organosilicone surfactant.

In some embodiments, the formulation can be in the form of a single package formulation including (a), (b), and (c), and further including at least one additive.

The formulation can also be in the form of a two-package or three-package formulation. For example, the formulation can be in the form of a two-package formulation, wherein the first package contains a mixture of two components selected from (a), (b), and (c), and optionally at least one additive, while the second package contains the third component selected from (a), (b), and (c) not included in the first package, and optionally at least one additive. The formulation can be in the form of a three-package formulation, wherein the first package contains (a) and optionally at least one additive, the second package contains (b) and optionally at least one additive, and the third package contains (c) and optionally at least one additive.

In some embodiments of the two-package or three-package formulation, the formulations containing (a), (b), (c), and optionally one or more additives are mixed before application and then applied simultaneously. In some embodiments, the mixing is performed as a tank mix (i.e., the formulations are mixed immediately before or upon dilution with water). In some embodiments, the one or more of the formulations are not mixed but are applied sequentially (in succession), for example, immediately or within 1 hour, within 2 hours, within 4 hours, within 8 hours, within 16 hours, within 24 hours, within 2 days, or within 3 days, of each other.

In some embodiments, the formulation of (a), (b), and (c) is present in suspended, emulsified, or dissolved form. Exemplary formulations include, but are not limited to, aqueous solutions, suspensions, also highly-concentrated aqueous, oily or other suspensions or dispersions, aqueous emulsions, aqueous microemulsions, aqueous suspo-emulsions, oil dispersions, and pastes.

In some embodiments, (a) aminopyralid or an agriculturally acceptable salt or ester thereof and/or (b) triclopyr or an agriculturally acceptable salt or ester thereof and/or (c) the organosilicone surfactant is an aqueous solution that can be diluted before use. In some embodiments, (a) and/or (b) and/or (c) is provided as a high-strength formulation such as a concentrate. In some embodiments, the concentrate is stable and retains potency during storage and shipping. In some embodiments, the concentrate is a clear, homogeneous liquid that is stable at temperatures of 54° C. or greater. In some embodiments, the concentrate does not exhibit any precipitation of solids at temperatures of −10° C. or higher. In some embodiments, the concentrate does not exhibit separation, precipitation, or crystallization of any components at low temperatures. For example, the concentrate remains a clear solution at temperatures below 0° C. (e.g., below −5° C., below −10° C., below −15° C.). In some embodiments, the concentrate exhibits a viscosity of less than 50 centipoise (50 megapascals), even at temperatures as low as 5° C.

The compositions and methods disclosed herein can also be mixed with or applied with an additive. In some embodiments, the additive can be diluted in water or can be concentrated. In some embodiments, the additive is added sequentially. In some embodiments, the additive is added simultaneously. In some embodiments, the additive is premixed with the aminopyralid or agriculturally acceptable salt thereof. In some embodiments, the additive is premixed with the triclopyr or agriculturally acceptable salt or ester thereof. In some embodiments, the additive is premixed with the organosilicone surfactant. In some embodiments, the additive is premixed with the aminopyralid or agriculturally acceptable salt or ester thereof and/or the triclopyr or agriculturally acceptable salt or ester thereof and/or the organosilicone surfactant.

In some embodiments, the additive is an additional pesticide. Exemplary additional pesticides include, but are not limited to, 2,4-D, acetochlor, aclonifen, amicarbazone, 4-aminopicolinic acid based herbicides, such as halauxifen, halauxifen-methyl, and others described in U.S. Pat. Nos. 7,314,849 and 7,432,227 to Balko, et al., amidosulfuron, aminocyclopyrachlor, aminotriazole, ammonium thiocyanate, asulam, atrazine, beflubutamid, benazolin, bensulfuron-methyl, bentazone, bifenox, bromacil, bromoxynil, butachlor, butafenacil, butralin, butroxydim, carbetamide, carfentrazone, carfentrazone-ethyl, chlormequat, clopyralid, chlorsulfuron, chlortoluron, cinidon-ethyl, clethodim, clodinafop-propargyl, clomazone, cyanazine, cyclosulfamuron, cycloxydim, cyhalofop-butyl, dicamba, dichlobenil, dichlorprop-P, diclofop-methyl, diclosulam, diflufenican, diflufenzopyr, dimefuron, dimethachlor, diquat, diuron, s-ethyl N,N-dipropylcarbamothioate (EPTC), ethoxysulfuron, fenoxaprop, fenoxaprop-ethyl, fenoxaprop-ethyl+isoxidifen-ethyl, fenoxaprop-P-ethyl, fenoxasulfone, flazasulfuron, florasulam, fluazifop, fluazifop-P-butyl, flucarbazone, flucarbazone-sodium, flucetosulfuron (LGC-42153), flufenacet, flumetsulam, flumioxazin, flupyrsulfuron, fluorochloridone, fluoroxypyr, fluoroxypyr-meptyl, flurtamone, glufosinate, glufosinate-ammonium, glyphosate, haloxyfop-methyl, haloxyfop-R, hexazinone, imazamethabenz, imazamox, imazapic, imazapyr, imazaquin, imazethapyr, imazosulfuron, indanofan, indaziflam, iodosulfuron, iodo-sulfuron-ethyl-sodium, ioxynil, isoproturon, isoxaben, isoxaflutole, lactofen, linuron, MCPA, MCPB, mecoprop-P, mesosulfuron, mesosulfuron-ethyl sodium, metazochlor, metosulam, metribuzin, metsulfuron, metsulfuron-methyl, MSMA, napropamide, napropamide-M, norfurazon, ortho-sulfamuron, oryzalin, oxadiargyl, oxadiazon, oxyfluorfen, paraquat, pendimethalin, penoxsulam, picloram, picolinafen, pinoxaden, primisulfuron, profluazol, propaquizafop, propoxycarbazone, propyzamide, prosulfocarb, prosulfuron, pyraflufen-ethyl, pyrasulfotole, pyribenzoxim (LGC-40863), pyroxsulam, pyroxasulfone, quinmerac, quizalofop-ethyl-D, quizalofop-P-ethyl, quizalofop-P-tefuryl, rimsulfuron, sethoxydim, simazine, sulfentrazone, sulfometuron, sulfosate, sulfosulfuron, tebuthiuron, tepraloxidim, terbacil, terbuthylazine, terbutryn, thiazopyr, thifensulfuron, thifensulfuron-methyl, topramezone, tralkoxydim, triasulfuron, tribenuron, tribenuron-methyl, triafamone, triclopyr, and trifluralin, and agriculturally acceptable salts, esters and mixtures thereof. In some embodiments, the additional pesticide includes clopyralid, fluoroxypyr, metsulfuron-methyl, 2,4-dichlorophenoxyacetic acid (2,4-D), dicamba, dichlorprop-P, halauxifen, halauxifen-methyl, 2-methyl-4-chlorophenoxyacetic acid (MCPA), penoxsulam, picloram, propanil, pyraflufen-ethyl, sulfentrazone, and combinations thereof.

In some embodiments, the aminopyralid or an agriculturally acceptable salt or ester thereof is provided in a premixed formulation with an additional pesticide. In some embodiments, the aminopyralid or an agriculturally acceptable salt or ester thereof is premixed with and/or co-packaged with, clopyralid, fluoroxypyr, metsulfuron-methyl, 2,4-dichlorophenoxyacetic acid (2,4-D), or combinations thereof. Exemplary premixes and co-packs of aminopyralid or agriculturally acceptable salts or esters thereof and an additive that are or have been commercially available include, but are not limited to, SENDERO® (a premix incorporating clopyralid by Dow AgroSciences LLC), CLEANWAVE® (a premix incorporating fluoroxypyr by Dow AgroSciences LLC), CHAPARRAL® (a premix incorporating metsulfuron-methyl by Dow AgroSciences LLC), CLEARVIEW® (a premix incorporating metsulfuron-methyl by Dow AgroSciences LLC), FOREFRONT R&P® (a co-pack incorporating 2,4-D by Dow AgroSciences LLC), GRAZONNEXT® (a co-pack incorporating 2,4-D by Dow AgroSciences LLC), PASTURALL® (a co-pack incorporating 2,4-D by Dow AgroSciences LLC), and RESTORE® (a co-pack incorporating 2,4-D by Dow AgroSciences LLC).

In some embodiments, the triclopyr or an agriculturally acceptable salt or ester thereof is provided in a premixed formulation with an additional pesticide. In some embodiments, the triclopyr or an agriculturally acceptable salt or ester thereof is premixed with clopyralid, 2,4-D, dicamba, dichlorprop-P, fluoroxypyr, metsulfuron-methyl, 2-methyl-4-chlorophenoxyacetic acid (MCPA), penoxsulam, picloram, propanil, pyraflufen-ethyl, sulfentrazone, and combinations thereof. Exemplary premixes of triclopyr or agriculturally acceptable salts or esters thereof and an additive that are or have been commercially available include, but are not limited to BRAZEN® (a premix incorporating clopyralid by Nufarm Americas, Inc.), CONFRONT® (a premix incorporating clopyralid by Dow AgroSciences LLC), REDEEM® (a premix incorporating clopyralid by Dow AgroSciences LLC), AQUASWEEP® (a premix incorporating 2,4-D by Nufarm Americas, Inc.), CANDOR® (a premix incorporating 2,4-D by Nufarm Americas, Inc.), CHASER® (a premix incorporating 2,4-D by Loveland Products, Inc.), CROSSBOW L® (a premix incorporating 2,4-D by Loveland Products, Inc.), 4-SPEED XT® (a premix incorporating 2,4-D, dicamba, and pyraflufen-ethyl by Nufarm Americas, Inc.), FOUNDATION® (a premix incorporating 2,4-D, dicamba, and sulfentrazone by Wilbur-Ellis Co.), T-ZONE® (a premix incorporating 2,4-D, dicamba, and sulfentrazone by PBI/Gordon Corp.), COOL POWER® (a premix incorporating dicamba and MCPA by Nufarm Americas, Inc.), HORSEPOWER® (a premix incorporating dicamba and MCPA by Nufarm Americas, Inc.), PROGENY® (a premix incorporating dicamba and MCPA by Nufarm Americas, Inc.), VENGEANCE PLUS® (a premix incorporating dichlorprop-P and MCPA by Wilbur-Ellis Co.), WIL-POWER® (a premix incorporating dichlorprop-P and MCPA by Wilbur-Ellis Co.), PASTUREGARD® (a premix incorporating fluoroxypyr by Dow AgroSciences LLC), TAILSPIN® (a premix incorporating fluoroxypyr by Loveland Products, Inc. and United AgriProducts), ULTIMATE® (a premix incorporating metsulfuron-methyl by Zelam Ltd.), GRASP XTRA® (a premix incorporating penoxsulam by Dow AgroSciences LLC), VICTORY GOLD® (a premix incorporating picloram by Zelam Ltd.), ATALAR® (a premix incorporating propanil by RiceCo LLC), CRYSTALPYR® (a premix incorporating propanil by Dupocsa, Protectores Quimicos para el Campo S.A.), and RICEPYR® (a premix incorporating propanil by RiceCo LLC).

In some embodiments, the additive includes an agriculturally acceptable adjuvant. Exemplary agriculturally acceptable adjuvants include, but are not limited to, antifreeze agents, antifoam agents, compatibilizing agents, sequestering agents, neutralizing agents and buffers, corrosion inhibitors, colorants, odorants, penetration aids, wetting agents, spreading agents, dispersing agents, thickening agents, freeze point depressants, antimicrobial agents, crop oil, safeners, adhesives (for instance, for use in seed formulations), surfactants, protective colloids, emulsifiers, tackifiers, and mixtures thereof. Exemplary agriculturally acceptable adjuvants include, but are not limited to, crop oil concentrate (mineral oil (85%)+emulsifiers (15%)), nonylphenol ethoxylate, benzylcocoalkyldimethyl quaternary ammonium salt, blend of petroleum hydrocarbon, alkyl esters, organic acid, and anionic surfactant, $C_9$-$C_{11}$ alkylpolyglycoside, phosphate alcohol ethoxylate, natural primary alcohol ($C_{12}$-$C_{16}$) ethoxylate, di-sec-butylphenol EO-PO block copolymer, polysiloxane-methyl cap, nonylphenol ethoxylate+urea ammonium nitrate, emulsified methylated seed oil, tridecyl alcohol (synthetic) ethoxylate (8 EO), tallow amine ethoxylate (15 EO), and PEG (400) dioleate-99.

In some embodiments, the additive is a safener that is an organic compound leading to better crop plant compatibility when applied with a herbicide. In some embodiments, the safener itself is herbicidally active. In some embodiments, the safener acts as an antidote or antagonist in the crop plants and can reduce or prevent damage to the crop plants. Exemplary safeners include, but are not limited to, AD-67 (MON 4660), benoxacor, benthiocarb, brassinolide, cloquintocet (mexyl), cyometrinil, cyprosulfamide, daimuron, dichlormid, dicyclonon, dietholate, dimepiperate, disulfoton, fenchlorazole, fenchlorazole-ethyl, fenclorim, flurazole, fluxofenim, furilazole, harpin proteins, isoxadifen-ethyl, jiecaowan, jiecaoxi, mefenpyr, mefenpyr-diethyl, mephenate, naphthalic anhydride, 2,2,5-trimethyl-3-(dichloroacetyl)-1,3-oxazolidine, 4-(dichloroacetyl)-1-oxa-4-azaspiro [4.5]decane, oxabetrinil, R29148, and N-phenyl-sulfonylbenzoic acid amides, as well as agriculturally acceptable salts thereof and, provided they have a carboxyl group, their agriculturally acceptable derivatives. In some embodiments, the safener can be cloquintocet or an ester or salt thereof, such as cloquintocet (mexyl).

Exemplary additional surfactants (e.g., wetting agents, tackifiers, dispersants, emulsifiers) include, but are not limited to, the alkali metal salts, alkaline earth metal salts and ammonium salts of aromatic sulfonic acids, for example lignosulfonic acids, phenolsulfonic acids, naphthalenesulfonic acids, and dibutylnaphthalenesulfonic acid, and of fatty acids, alkyl- and alkylarylsulfonates, alkyl sulfates, lauryl ether sulfates and fatty alcohol sulfates, and salts of sulfated hexa-, hepta- and octadecanols, and also of fatty alcohol glycol ethers, condensates of sulfonated naphthalene and its derivatives with formaldehyde, condensates of naphthalene or of the naphthalene sulfonic acids with phenol and formaldehyde, polyoxyethylene octylphenol ether, ethoxylated isooctyl-, octyl- or nonylphenol, alkylphenyl or tributylphenyl polyglycol ether, alkyl aryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignosulfite waste liquors and proteins, denatured proteins, polysaccharides (e.g., methylcellulose), hydrophobically modified starches, polyvinyl alcohol, polycarboxylates, polyalkoxylates, polyvinyl amine, polyethyleneimine, polyvinylpyrrolidone and copolymers thereof.

Exemplary thickeners include, but are not limited to, polysaccharides, such as xanthan gum, and organic and inorganic sheet minerals, and mixtures thereof.

Exemplary antifoam agents include, but are not limited to, silicone emulsions, long-chain alcohols, fatty acids, salts of fatty acids, organofluorine compounds, and mixtures thereof.

Exemplary antimicrobial agents include, but are not limited to, bactericides based on dichlorophen and benzyl alcohol hemiformal, and isothiazolinone derivates, such as alkylisothiazolinones and benzisothiazolinones, and mixtures thereof.

Exemplary antifreeze agents, include, but are not limited to ethylene glycol, propylene glycol, urea, glycerol, and mixtures thereof.

Exemplary colorants include, but are not limited to, the dyes known under the names Rhodamine B, pigment blue 15:4, pigment blue 15:3, pigment blue 15:2, pigment blue 15:1, pigment blue 80, pigment yellow 1, pigment yellow 13, pigment red 112, pigment red 48:2, pigment red 48:1, pigment red 57:1, pigment red 53:1, pigment orange 43, pigment orange 34, pigment orange 5, pigment green 36, pigment green 7, pigment white 6, pigment brown 25, basic violet 10, basic violet 49, acid red 51, acid red 52, acid red 14, acid blue 9, acid yellow 23, basic red 10, basic red 108, and mixtures thereof.

Exemplary adhesives include, but are not limited to, polyvinylpyrrolidone, polyvinyl acetate, polyvinyl alcohol, tylose, and mixtures thereof.

In some embodiments, the additive includes a carrier. In some embodiments, the additive includes a liquid carrier. In some embodiments, the additive includes an organic or inorganic carrier. Exemplary liquid carriers include, but are not limited to, petroleum fractions or hydrocarbons such as mineral oil, aromatic solvents, paraffinic oils, and the like or less, vegetable oils such as soybean oil, rapeseed oil, olive oil, castor oil, sunflower seed oil, coconut oil, corn oil, cottonseed oil, linseed oil, palm oil, peanut oil, safflower oil, sesame oil, tung oil and the like or less, esters of the above vegetable oils or less, esters of monoalcohols or dihydric, trihydric, or other lower polyalcohols (4-6 hydroxy containing), such as 2-ethyl hexyl stearate, n-butyl oleate, isopropyl myristate, propylene glycol dioleate, di-octyl succinate, di-butyl adipate, di-octyl phthalate and the like or less, esters of mono, di and polycarboxylic acids and the like, toluene, xylene, petroleum naphtha, crop oil, acetone, methyl ethyl ketone, cyclohexanone, trichloroethylene, perchloroethylene, ethyl acetate, amyl acetate, butyl acetate, propylene glycol monomethyl ether and diethylene glycol monomethyl ether, methyl alcohol, ethyl alcohol, isopropyl alcohol, amyl alcohol, ethylene glycol, propylene glycol, glycerine, N-methyl-2-pyrrolidinone, N,N-dimethyl alkylamides, dimethyl sulfoxide, liquid fertilizers and the like, and water as well as mixtures thereof.

In some embodiments, emulsions, pastes or oil dispersions, can be prepared by homogenizing (a), (b), and (c) in water, optionally by means of wetting agent, tackifier, dispersant or emulsifier. In some embodiments, concentrates suitable for dilution with water are prepared, comprising (a), (b), (c), and optionally a wetting agent, a tackifier, and/or a dispersant or emulsifier.

In some embodiments, the concentrations of (a), (b), and (c) in the formulations can be varied. In some embodiments, the formulations comprise from 1% to 95% (e.g., from 5% to 95%, from 10% to 80%, from 20% to 70%, from 30% to 50%) by total weight of (a), (b), and (c). In some embodiments, (a), (b), and (c) independently, can be employed in a purity of from 90% to 100% (e.g., from 95% to 100%) according to nuclear magnetic resonance (NMR) spectrometry. In some embodiments, the concentrations of (a), (b), (c) and additional pesticides in the formulations can be varied. In some embodiments, the formulations comprise from 1% to 95% (e.g., from 5% to 95%, from 10% to 80%, from 20% to 70%, from 30% to 50%) by total weight of (a), (b), (c), and additional pesticides. In some embodiments, (a), (b), (c) and additional pesticides, independently, can be employed in a purity of from 90% to 100% (e.g., from 95% to 100%) according to NMR spectrometry.

Methods of Application

The compositions disclosed herein can be applied in any known technique for applying herbicides. Exemplary application techniques include, but are not limited to, spraying, atomizing, or direct application into water (in-water). The method of application can vary depending on the intended purpose. In some embodiments, the method of application can be chosen to ensure the finest possible distribution of the compositions disclosed herein.

The compositions disclosed herein can be applied pre-emergence (before the emergence of undesirable vegetation) or post-emergence (i.e., during and/or after emergence of the undesirable vegetation). In certain cases, the compositions are applied post-emergence. When the compositions are used in crops, the compositions can be applied after seeding and before or after the emergence of the crop plants. In some embodiments, the compositions disclosed herein show good crop tolerance even when the crop has already emerged, and can be applied during or after the emergence of the crop plants. In some embodiments, when the compositions are used in crops, the compositions can be applied before seeding of the crop plants.

In some embodiments, the compositions disclosed herein are applied to vegetation or an area adjacent the vegetation or applied to soil or water to prevent the emergence or growth of vegetation by spraying (e.g., foliar spraying). In some embodiments, the spraying techniques use, for example, water as carrier and spray liquor rates of from 0.5 liters per hectare (L/ha) to 2000 L/ha (e.g., from 0.5 L/ha to 50 L/ha, from 50 L/ha to 1000 L/ha, or from 100 to 500 L/ha). In some embodiments, wherein the compositions disclosed herein are less well tolerated by certain crop plants, the compositions can be applied with the aid of the spray apparatus in such a way that they come into little contact, if any, with the leaves of the sensitive crop plants while reaching the leaves of undesirable vegetation that grows underneath or the bare soil (e.g., post-directed or lay-by).

In some embodiments, herbicidal activity is exhibited by the compounds of the synergistic mixture when they are applied directly to the plant or to the locus of the plant at any stage of growth or before planting or emergence. The effect observed can depend upon the type of undesirable vegetation to be controlled, the stage of growth of the undesirable vegetation, the application parameters of dilution and spray drop size, the environmental conditions at the time of use, the specific compound employed, the specific adjuvants and carriers employed, the soil type, and the like, as well as the amount of chemical applied. In some embodiments, these and other factors can be adjusted to promote non-selective or selective herbicidal action.

The compositions and methods disclosed herein can be used to control undesired vegetation in a variety of crop and non-crop applications.

In some embodiments, the compositions and methods disclosed herein can be used for controlling undesired vegetation in rice (e.g., in flooded seeded rice, in flooded transplanted rice, or in rice seedbeds prior to planting rice seeds or rice transplants). In these cases, the composition can be applied, for example, to the vegetation as an in-water application to a flooded rice field.

The compositions and methods disclosed herein can be used in crop plants that are resistant to, for instance, herbicides, pathogens, and/or insects. In some embodiments, the compositions and methods disclosed herein can be used in crop plants that are resistant to one or more herbicides because of genetic engineering or breeding. In some embodiments, the compositions and methods disclosed herein can be used in crop plants that are resistant to one or more pathogens such as plant pathogenous fungi owing to genetic engineering or breeding. In some embodiments, the compositions and methods disclosed herein can be used in crop plants that are resistant to attack by insects owing to genetic engineering or breeding.

In some embodiments, the crop is rice that is resistant to synthetic auxins, or rice that, owing to introduction of the gene for *Bacillus thuringiensis* (or Bt) toxin by genetic modification, is resistant to attack by certain insects. In some embodiments, the compositions and methods described herein also can be used in conjunction with glyphosate, glufosinate, dicamba, phenoxy auxins, pyridyloxy auxins, aryloxyphenoxypropionates, acetyl CoA carboxylase (AC-Case) inhibitors, imidazolinones, acetolactate synthase (ALS) inhibitors, 4-hydroxyphenyl-pyruvate dioxygenase (HPPD) inhibitors, protoporphyrinogen oxidase (PPO) inhibitors, triazines, and bromoxynil to control vegetation in rice that is tolerant to glyphosate, glufosinate, dicamba, phenoxy auxins, pyridyloxy auxins, aryloxyphenoxypropionates, acetyl CoA carboxylase (ACCase) inhibitors, imidazolinones, acetolactate synthase (ALS) inhibitors, 4-hydroxyphenyl-pyruvate dioxygenase (HPPD) inhibitors, protoporphyrinogen oxidase (PPO) inhibitors, triazines, bromoxynil, or combinations thereof. In some embodiments, the undesirable vegetation is controlled in glyphosate, glufosinate, dicamba, phenoxy auxins, pyridyloxy auxins, aryloxyphenoxypropionates, acetyl CoA carboxylase (ACCase) inhibitors, imidazolinones, acetolactate synthase (ALS) inhibitors, 4-hydroxyphenyl-pyruvate dioxygenase (HPPD) inhibitors, protoporphyrinogen oxidase (PPO) inhibitors, triazines, and bromoxynil tolerant rice possessing multiple or stacked traits conferring tolerance to multiple chemistries and/or multiple modes of action. The combination of (a), (b), and (c), can be used in combination with herbicides that are selective for the crop (e.g., rice) being treated, and which complement the spectrum of weeds controlled by these compositions at the application rate employed.

Exemplary non-crop areas include, but are not limited to, turfgrass, pastures, grasslands, rangelands, fallow land, rights-of-way, aquatic settings, tree and vine, wildlife management areas, non-irrigation ditchbanks, and forests. In some embodiments, the compositions and methods disclosed herein can be used in industrial vegetation management (IVM), for example, to control undesired vegetation along roadsides, power-lines, pipelines, rights-of-way, railways, well sites, and equipment yards. In some embodiments, the compositions and methods disclosed herein can also be used in forestry (e.g., for site preparation or for combating undesirable vegetation in plantation forests). In some embodiments, the compositions and methods disclosed herein can be used to control undesirable vegetation in conservation reserve program lands (CRP), trees, vines, grasslands, and grasses grown for seed. In some embodiments, the compositions and methods disclosed herein can be used on lawns (e.g., residential, industrial, and institutional), golf courses, parks, cemeteries, athletic fields, and sod farms.

The herbicidal compositions prepared disclosed herein are effective against a variety of types of undesirable vegetation. In some embodiments, the compositions disclosed herein can be used for controlling broadleaf weeds, sedge weeds, woody plants, semi-woody plants, and combinations thereof. In some cases, the undesirable vegetation is selected from gorse (*Ulex europaeus*, ULEEU), blackthorn (*Prunus spinosa*, PRNSN, also referred to as sloe), species of ash (*Fraxinus* sp., FRXSS), bloody-twig dogwood (*Cornus sanguine*, CRWSA), species of the genus *Carex* (*Carex* sp., CRXSS), Scotch broom (*Cytisus scoparius*, SAOSC), common hawthorn (*Crataegus monogina*, CSCMO), and combinations thereof.

The compositions and methods disclosed herein can be used to control undesired vegetation over an extended period of time. In some embodiments, the compositions and methods disclosed herein can be used to control undesired vegetation (e.g., to provide at least 70% control, to provide at least 75% control, to provide at least 80% control, to provide at least 85% control, to provide at least 90% control, or to provide at least 95% control) for a period of at least 180 days after application (e.g., for a period of at least 210 days, for a period of at least 240 days, for a period of at least 270 days, for a period of at least 300 days, for a period of at least 330 days, for a period of at least 365 days, or longer).

By way of non-limiting illustration, examples of certain embodiments of the present disclosure are given below.

EXAMPLES

Evaluation of Applications of Aminopyralid, Triclopyr, and a Polyalkyleneoxide-Modified Heptamethyltrisiloxane Surfactant for Weed Control Field trials were conducted with applications made in the area of naturally occurring woody and semi-woody plant populations. Treatments were applied post emergence to the woody and semi-woody plants. All treatments were applied using a randomized complete block trial design, with four replications per treatment.

Treatments consisted of aminopyralid and triclopyr, applied alone or in combination with polyalkyleneoxide-modified heptamethyltrisiloxane (SILWET® L-77) Aminopyralid and triclopyr were provided as premixed compositions (GF-1883 and GF-1365, see Table 1).

TABLE 1

Composition of GF-1883 and GF-1365.

| Composition | Active Ingredients | Concentration (g ai/L) | Concentration (ai % by weight) | Concentration (g ae/L) | Concentration (ae % by weight) |
|---|---|---|---|---|---|
| GF-1883 | aminopyralid-triisopropanolammonium | 23.08 | 2.22% w/w | 12 | 1.15% w/w |
|  | triclopyr-triethylammonium | 167.36 | 16.09% w/w | 120 | 11.54% w/w |
| GF-1365 | aminopyralid-potassium | 35.507 | 2.22% w/w | 12 | 1.15% w/w |
|  | triclopyr-butotyl | 333.567 | 16.09% w/w | 120 | 11.54% w/w | g ai/L = grams active ingredient per liter
ai % by weight = active ingredient percent by weight
w/w = weight per weight
g ae/L = grams acid equivalent ingredient per liter
ae % by weight = acid equivalent percent by weight GF-1883 and/or GF-1365, alone or in combination with SILWET® L-77, were applied to the target plants at a spray volume of either 800 or 1,000 L/ha and at varying weed stages (see Table 2). Compositions were applied with a lance directed at the targeted plant at a height of approximately 1.0 to 1.5 meters (m) from the soil.

TABLE 2

Spray volume and weed stage at application.

| Trial | Targeted Weed | Spray Volume (L/ha) | Weed Stage at Application |
|---|---|---|---|
| 1 | *Cytisus scoparius*, SAOSC | 1,000 | 1 m height |
| 2 | *Cytisus scoparius*, SAOSC | 1,000 | B35-39 |
| 3 | *Ulex europeus*, ULEEU | 1,000 | B30 |
| 4 | *Carex* sp., CRXSS | 800 | 80 centimeters (cm) height |
| 5 | *Prunus spinosa*, PRNSN | 1,000 | B35 |
| 6 | *Cytisus scoparius*, SAOSC | 1,000 | 1.20 m height |
| 7 | *Ulex europeus*, ULEEU | 800 | 80 cm height |
| 8 | *Fraxinus* sp., FRXSS | 1,000 | B39 |
| 9 | *Prunus spinosa*, PRNSN | 1,000 | 1.20 m height |
| 10 | *Fraxinus* sp., FRXSS | 1,000 | 90 cm height |
| 11 | *Fraxinus* sp., FRXSS | 1,000 | B35 |

The average percent control of several species of targeted plants (indicated by Bayer codes) at 1 year after treatment are provided in Table 3 below. The treated plots and control plots were visually rated blind at one year after application. Ratings were based on a scale of 0-100%, as discussed above, wherein 0% indicates complete growth of the undesired vegetation and 100% indicates complete prevention of the undesired vegetation. The results are included in Table 3 below.

TABLE 3

Average Percent Weed Control at 1 Year after Treatment

| Treatment | Application Rate L/ha | Average Percent (%) Weed Control at 1 Year after Treatment | | | | |
|---|---|---|---|---|---|---|
| | | PRNSN | FRXSS | SAOSC | CRXSS | ULEEU |
| GF-1883 | 2 | 41.7 | 47.2 | 92.6 | 48.3 | 62.2 |
| GF-1883 + SILWET® L-77 | 2 0.1 | 88.0 | 81.6 | 98.7 | 66.7 | 92.5 |
| GF-1365 | 1 | — | 60.8 | — | — | — |
| GF-1365 + SILWET® L-77 | 1 0.1 | — | 79.8 | — | — | — |

The application of SILWET® L-77 in conjunction with GF-1883 increased the average percent weed control at 1 year after treatment by approximately 30% against ULEEU (two trials conducted), approximately 47% against PRNSN (two trials conducted), approximately 35% against FRXSS (three trials conducted), approximately 18% against CRXSS (one trial conducted), and approximately 6% against SAOSC (three trials conducted) relative to treatment with GF-1883 alone. The application of SILWET® L-77 in conjunction with GF-1365 increased the average percent weed control at 1 year after treatment of the GF-1365 by approximately 19% against FRXSS (three trials conducted) relative to treatment with GF-1365 alone.

Comparison of a Polyalkyleneoxide-Modified Heptamethyltrisiloxane Surfactant with other Surfactants The efficacy of compositions containing aminopyralid, triclopyr, and a polyalkyleneoxide-modified heptamethyltrisiloxane surfactant was compared to the efficacy of compositions containing aminopyralid, triclopyr, and a non-organosilicone surfactant. Non-organosilicone surfactants tested included a soy-derived, non-ionic penetrating surfactant (a mixture of phosphatidylcholine, methylacetic acid and an alkyl polyoxyethylene ether, which is or was commercially available under the trademark LI 700® by Loveland Products, Inc.), a surfactant including self-emulsifiable esters of rapeseed oil (which is or was commercially available under the trademark ACRIROB® B by Bayer CropScience), and a non-ionic surfactant including a mixture of alcohol ethoxylates and natural fatty acids (which is or was commercially available under the trademark ACTIVATOR 90® by Loveland Products, Inc.).

Field trials were conducted with applications made in the area of naturally occurring woody and semi-woody plant populations. Treatments were applied post emergence to the woody and semi-woody plants. All treatments were applied using a randomized complete block trial design, with four replications per treatment.

Treatments consisted of aminopyralid and triclopyr, applied alone or in combination with a surfactant (SILWET® L-77, LI 700®, ACRIROB® B, or ACTIVATOR 90®). Aminopyralid and triclopyr were provided as pre-mixed compositions (GF-1883 and GF-1365, see Table 1 above). Compositions were applied to the target plants at a spray volume of either 800 or 1,000 L/ha and at varying weed stages (see Table 2). Compositions were applied with a lance directed at the targeted plant at a height of approximately 1.0 to 1.5 m from the soil.

The average percent control of several species of targeted plants (indicated by Bayer codes) at 1 year after treatment are provided in Table 4 below. The treated plots and control plots were visually rated blind at one year after application. Ratings were based on a scale of 0-100%, as discussed above, wherein 0% indicates complete growth of the undesired vegetation and 100% indicates complete prevention of the undesired vegetation. The results are included in Table 4 below.

TABLE 4

Average Percent Weed Control at 1 Year after Treatment

| Treatment | Application Rate L/ha | Average Percent (%) Weed Control at 1 Year after Treatment | |
|---|---|---|---|
| | | PRNSN | FRXSS |
| GF-1883 | 2 | 26.7 | 31.7 |
| GF-1883 + SILWET ® L-77 | 2 0.1 | 87.7 | 75.5 |
| GF-1883 + LI 700 ® | 2 0.5 | 40.0 | — |
| GF-1883 + ACTIROB B ® | 2 0.5 | 76.7 | — |
| GF-1883 + ACTIVATOR 90 ® | 2 0.1 | — | 42.5 |
| GF-1365 | 1 | — | 45.8 |
| GF-1365 + SILWET ® L-77 | 1 0.1 | — | 73.0 |
| GF-1365 + ACTIVATOR 90 ® | 1 0.1 | — | 44.2 |

The application of SILWET® L-77 in conjunction with GF-1883 increased the average percent weed control at 1 year after treatment by approximately 60% against PRNSN (one trial conducted) relative to treatment with GF-1883 alone. In contrast, application of LI 700® in conjunction with GF-1883 only increased the average percent weed control at 1 year after treatment by approximately 14% against PRNSN (one trial conducted) relative to treatment with GF-1883 alone. Application of ACTIROB B® in conjunction with GF-1883 only increased the average percent weed control at 1 year after treatment of the GF-1883 by approximately 50% relative to treatment with GF-1883 alone.

Similarly, the application of SILWET® L-77 in conjunction with GF-1883 increased the average percent weed control at 1 year after treatment by approximately 40% against FRXSS (two trials conducted) relative to treatment with GF-1883 alone. The application of SILWET® L-77 in conjunction with GF-1365 increased the average percent weed control at 1 year after treatment by approximately 30% against FRXSS (two trials conducted) relative to treatment with GF-1365 alone. In contrast, application of ACTIVATOR 90® in conjunction with GF-1883 or GF-1365 resulted in no significant or only a slight increase in the average percent weed control at 1 year after treatment against FRXSS (two trials conducted) relative to treatment with GF-1883 or GF-1365 alone.

The compositions and methods of the appended claims are not limited in scope by the specific compositions and methods described herein, which are intended as illustrations of a few aspects of the claims and any compositions and methods that are functionally equivalent are intended to fall within the scope of the claims. Various modifications of the compositions and methods in addition to those shown and described herein are intended to fall within the scope of the appended claims. Further, while only certain representative compositions and method steps disclosed herein are specifically described, other combinations of the compositions and method steps also are intended to fall within the scope of the appended claims, even if not specifically recited. Thus, a combination of steps, elements, components, or constituents may be explicitly mentioned herein or less, however, other combinations of steps, elements, components, and constituents are included, even though not explicitly stated. The term "comprising" and variations thereof as used herein is used synonymously with the term "including" and variations thereof and are open, non-limiting terms. Although the terms "comprising" and "including" have been used herein to describe various embodiments, the terms "consisting essentially of" and "consisting of" can be used in place of "comprising" and "including" to provide for more specific embodiments of the invention and are also disclosed. Other than in the examples, or where otherwise noted, all numbers expressing quantities of ingredients, reaction conditions, and so forth used in the specification and claims are to be understood at the very least, and not as an attempt to limit the application of the doctrine of equivalents to the scope of the claims, to be construed in light of the number of significant digits and ordinary rounding approaches.

What is claimed is:

1. A herbicidal composition comprising a herbicidal mixture and an organosilicone surfactant, wherein the herbicidal mixture consists of a herbicidal effective amount of (a) aminopyralid or an agriculturally acceptable salt or ester thereof, and (b) triclopyr or an agriculturally acceptable salt or ester thereof;
   wherein the acid equivalent weight ratio of (a) to (b) is from 1:2 to 1:20;
   wherein the weight ratio of the organosilicone surfactant (in g ai/ha) to (a) (in g ae/ha) and (b) (in g ae/ha) in combination is from 1:1 to 1:8; and
   wherein the organosilicone surfactant includes a polyalkyleneoxide-modified heptamethyltrisiloxane defined by Formula II

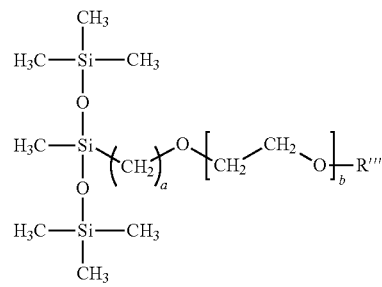

wherein
a is an integer ranging from 1 to 10;
b is an integer ranging from 1 to 30; and
R''' is hydrogen or a $C_1$-$C_4$ hydrocarbyl group.

2. The composition of claim 1, wherein the acid equivalent weight ratio of (a) to (b) is from 1:7 to 1:10.

3. The composition of claim 1, wherein (a) includes aminopyralid-triisopropanolammonium, aminopyralid-potassium, or combinations thereof.

4. The composition of claim 1, wherein (b) includes triclopyr-triethylammonium, triclopyr-butotyl, or combinations thereof.

5. The composition of claim 1, further comprising an agriculturally acceptable adjuvant.

6. The composition of claim 5, wherein the agriculturally acceptable adjuvant includes a herbicide safener.

7. A method of controlling undesirable vegetation which comprises applying to vegetation or an area adjacent the vegetation or applying to soil or water, a composition comprising a herbicidal mixture and an organosilicone surfactant, wherein the herbicidal mixture consists of a herbicidal effective amount of (a) aminopyralid or an agriculturally acceptable salt or ester thereof, and (b) triclopyr or an agriculturally acceptable salt or ester thereof;
   wherein the acid equivalent weight ratio of (a) to (b) is from 1:2 to 1:20;
   wherein the weight ratio of the organosilicone surfactant (in g ai/ha) to (a) (in g ae/ha) and (b) (in g ae/ha) in combination is from 1:1 to 1:8; and
   wherein the organosilicone surfactant includes a polyalkyleneoxide-modified heptamethyltrisiloxane defined by Formula II

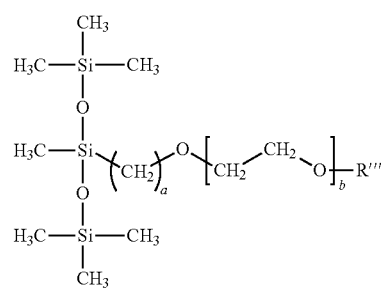

wherein
a is an integer ranging from 1 to 10;
b is an integer ranging from 1 to 30; and R''' is hydrogen or a $C_1$-$C_4$ hydrocarbyl group;
wherein (a) is applied in an amount of from 20-65 g ae/ha; and
wherein (b) is applied in an amount of from 200-400 g ae/ha.

8. The method of claim 7, wherein the acid equivalent weight ratio of (a) to (b) is from 1:7 to 1:10.

9. The method of claim 7, wherein (a) includes aminopyralid-triisopropanolammonium, aminopyralid-potassium, or combinations thereof.

10. The method of claim 7, wherein (b) includes triclopyr-triethylammonium, triclopyr-butotyl, or combinations thereof.

11. The method of claim 7, wherein the undesirable vegetation includes gorse, blackthorn, species of ash, bloody-twig dogwood, species of the genus *Carex*, Scotch broom, common hawthorn, and combinations thereof.

12. The method of claim 7, wherein the undesirable vegetation is controlled for a period of at least 180 days after application.

13. The method of claim 7, wherein (a) is applied in an amount of from 25-65 g ae/ha.

14. The method of claim 7, wherein (b) is applied in an amount of from 250-400 g ae/ha.

15. The method of claim 7, wherein the organosilicone surfactant is applied in an amount from 150-180 g ai/ha.

16. The method of claim 7, wherein the undesirable vegetation is controlled for a period of at least 365 days after application.

* * * * *